United States Patent [19]

Lang et al.

[11] Patent Number: 4,918,176

[45] Date of Patent: Apr. 17, 1990

[54] UNSATURATED CYCLOALIPHATIC DERIVATIVES

[75] Inventors: Gerard Lang, Saint-Gratien; Serge Forestier, Claye-Souilly; Alain Lagrange, Chatou, all of France

[73] Assignee: Societe Anonyme dite: L'Oreal, Paris, France

[21] Appl. No.: 831,552

[22] Filed: Feb. 20, 1986

[30] Foreign Application Priority Data

Feb. 20, 1985 [LU] Luxembourg ............................ 85777

[51] Int. Cl.$^4$ .................... C07H 15/00; C07D 265/30; C07C 47/52
[52] U.S. Cl. ..................................... 536/17.2; 536/4.1; 536/18.1; 536/22; 544/106; 544/224; 544/336; 548/400; 549/356; 558/411; 568/425; 568/715

[58] Field of Search ................. 568/425, 715; 536/4.1, 536/22, 17.2, 18.1; 544/106, 224, 336; 548/400; 549/356; 558/411

[56] References Cited

FOREIGN PATENT DOCUMENTS 2415616 8/1979 France .

OTHER PUBLICATIONS

Lang et al., Chemical Abstracts, vol. 104, 1986, No. 207482y.

*Primary Examiner*—Johnnie R. Brown
*Assistant Examiner*—Elli Peselev
*Attorney, Agent, or Firm*—Cushman, Darby & Cushman

[57] ABSTRACT

Unsaturated norbornane, 2,2-dimethyl norbornane, adamantane or cyclododecane derivatives exhibit activity in the systemic and topical treatment of dermatologic disorders.

19 Claims, No Drawings

UNSATURATED CYCLOALIPHATIC DERIVATIVES

The present invention relates to new unsaturated cycloaliphatic derivatives, to their preparation and to their use in therapeutic and cosmetic compositions.

The new unsaturated cycloaliphatic derivatives according to the present invention exhibit activity in the systemic and topical treatment of dermatologic diseases linked to a keratinization disorder (differentiation-proliferation), dermatologic diseases, or others, from inflammatory and/or immunoallergic components, in the treatment of degenerative diseases of conjunctive tissue, as well as an anti-tumor activity, and in the field of ophthamology for the treatment of corneopathies.

These new derivatives also are useful as an active agent or component in cosmetic compositions.

The unsaturated cycloaliphatic derivatives according to the present invention can be represened by the following formula

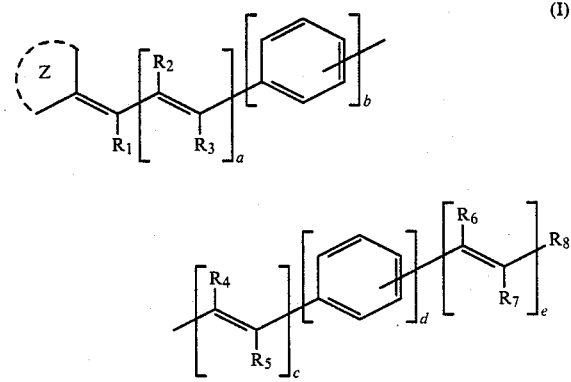

wherein $R_1$ to $R_7$, each independently, represent hydrogen, or lower alkyl, $R_8$ represents —C≡N, an oxazolinyl radical or a radical corresponding to one of the following formulas

wherein $R_9$ represents hydrogen, lower alkyl, cyclopentyl, cyclohexyl, mono-or polyhydroxyalkyl or a tetrahydropyrannyl radical and $R_{10}$ represents hydrogen, lower alkyl, —$OR_{11}$ or

wherein r' and r" each independently represent hydrogen, linear or branched alkyl, mono- or polyhydroxyalkyl, alkenyl, cyclopentyl, cyclohexyl, aryl or aralkyl optionally substituted, or taken together form a heterocycle, or r' represents hydrogen and r" represents the residue of an amino acid or glucosamine, $R_{11}$ represents hydrogen, alkyl, mono- or polyhydroxy lower alkyl, or the residue of a sugar, Z represents the residue of a saturated monocycloaliphatic radical having 8–12 carbon atoms, or a bi- or tri-cyclic radical, optionally substituted, the said radical Z not carrying any carbonyl function, a and e represent 0, 1 or 2, and b, c and d represent 0 or 1, it being understood that:

$a+c+e \geq 1$ and that b and/or d=1, and the geometric and optical isomers of the said compounds of formula I, as well as their salts.

By the expression alkyl radical is meant alkyl radicals having 1–18 carbon atoms and principally methyl, ethyl, propyl, 2-ethyl hexyl, octyl, dodecyl, hexadecyl and octadecyl radicals.

By the expression lower alkyl is meant radicals having from 1–4 carbon atoms and principally methyl, ethyl, isopropyl, butyl and tert. butyl radicals.

When $R_1$ to $R_7$ represent lower alkyl, preferably the lower alkyl is a methyl radical.

By the expression aryl is meant phenyl, optionally substituted by a halogen such as chlorine, bromine or fluorine, hydroxy, or lower alkoxy which is preferably methoxy, ethoxy or isopropoxy.

Representative aralkyl radicals include benzyl as well as phenethyl, optionally substituted by hydroxy or lower alkoxy.

By the expression alkenyl is meant an unsaturated radical having 2–18 carbon atoms, preferably 3–6 carbon atoms, and preferably propenyl, butenyl and isopentenyl.

By the expression monohydroxy lower alkyl is meant radicals having 2–3 carbon atoms and principally 2-hydroxyethyl and 2-hydroxypropyl.

By the expression polyhydroxyalkyl is meant a radical having 3–6 carbon atoms and 2–5 hydroxy groups such as 2,3-dihydroxy propyl, 2,3,4-trihydroxy butyl, 2,3,4,5-tetrahydroxy pentyl and the residue of pentaerythritol.

When the radicals r' and r" together form a heterocycle, the heterocycle can be piperidino, piperazino, morpholino, pyrrolidino or 4-(2-hydroxyethyl)piperazino.

By the expression residue of a sugar is meant a radical derived from a sugar such as glucose, mannitol, erythritol or galactose.

In accordance with the present invention the radical Z is preferably a cycloaliphatic residue derived from norbornane, 2,2-dimethyl norbornane, adamantane or cyclododecane.

When the compounds according to the present invention are provided in salt form, they are salts of zinc, an alkali or alkaline earth metal or of an organic amine when they carry at least one free acid function, or salts of a mineral or organic acid, principally hydrochlorides, hydrobromides or citrates when they carry at least one amine function.

Among the particularly preferred compounds of formula I according to the invention, are those corresponding to the following formulas:

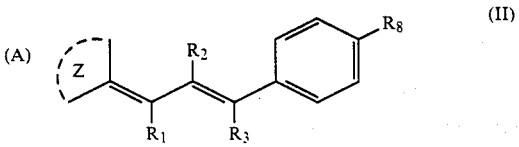

wherein $R_1$ and $R_3$ represent hydrogen, $R_2$ represents hydrogen or lower alkyl, $R_8$ represents

$R_{10}$ represents —$OR_{11}$ or

$R_{11}$ represents hydrogen, alkyl or hydroxy lower alkyl, r' and r'' represent hydrogen or lower alkyl, and Z represents a cycloaliphatic residue derived from norbornane, 2,2-dimethyl norbornane or adamantane;

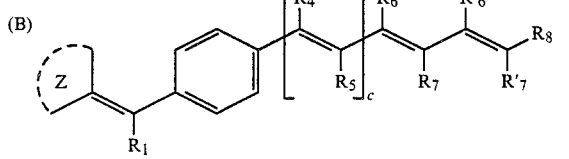

$R_1$, $R_5$, $R_6$, $R_7$ and $R'_7$ represent hydrogen,
$R_4$ represents lower alkyl,
$R'_6$ represents hydrogen or lower alkyl,
$R_8$ represents

$R_{10}$ represents —$OR_{11}$ or

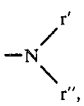

$R_{11}$ represents hydrogen, alkyl, hydroxy lower alkyl or the residue of a sugar, r' represents hydrogen and r'' represents lower alkyl or the residue of an amino acid, Z represents a cycloaliphatic residue derived from norbornane, adamantane or cyclododecane, and c is 0 or 1.

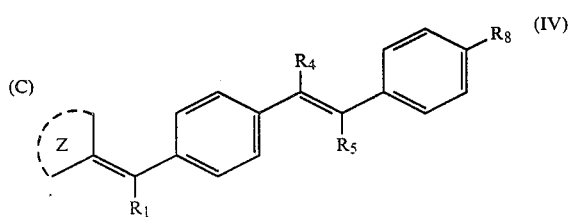

wherein
$R_1$ and $R_5$ represent hydrogen,
$R_4$ represents lower alkyl,
$R_8$ represents

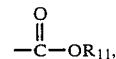

$R_{11}$ represents hydrogen, alkyl or hydroxy lower alkyl, and

Z represents a cycloaliphatic residue derived from admanatane.

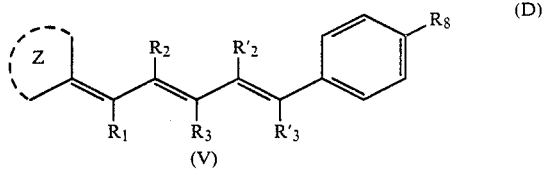

wherein
$R_1$, $R_2$, $R_3$ and $R'_3$ represent hydrogen,
$R'_2$ represents lower alkyl,
$R_8$ represents

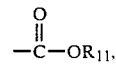

$R_{11}$ represents hydrogen, alkyl or hydroxy lower alkyl, and

Z represents a cycloaliphatic residue derived from 2,2-dimethyl norbornane.

Representative compounds of formula I include
(1) 3-[3-(4'-methoxy carbonyl phenyl)-2-propen]-ylidene-2,2-dimethyl norbornane,
(2) 3-[3-(4'-carboxy phenyl)-2-propen]-ylidene-2,2-dimethyl norbornane,
(3) 2-[3-(4'-methoxy carbonyl phenyl)-2-methyl-2-propen]-ylidene adamantane,
(4) 2-[3-(4'-carboxy phenyl)-2-methyl-2-propen]-ylidene adamantane,
(5) 2-[3-(4'-methoxy carbonyl phenyl)-2-methyl-2-propen]-ylidene norbornane,
(6) 2-[3-(4'-carboxyl phenyl)-2-methyl-2-propen]-ylidene norbornane,
(7) 4'-[4-ethoxycarbonyl-3-methyl-1,3-butadien]yl-2-benzylidene adamantane,
(8) 4'-[4-carboxy-3-methyl-1,3-butadien]yl-2-benzylidene adamantane,
(9) 4'-[4-ethoxycarbonyl-3-methyl-1,3-butadien]-yl-2-benzylidene norbornane,
(10) 4'-[4-carboxy-3-methyl-1,3-butadien]-yl-2-benzylidene norbornane,
(11) 2-[3-(4'-N-ethylamino carbonyl phenyl)-2-methyl-2-propen]-ylidene adamantane,
(12) 4'-[4-ethoxy carbonyl-3-methyl-1,3-butadien]-yl benzylidene cyclododecane,
(13) 4'-[4-carboxy-3-methyl-1,3-butadien]-yl benzylidene cyclododecane,
(14) 4'-[6-ethoxy carbonyl-1,5-dimethyl-1,3,5-hexatrien]-yl-2-benzylidene adamantane,
(15) 4'-[6-carboxy-1,5-dimethyl-1,3,5-hexatrien]-yl-2-benzylidene adamantane,
(16) 4'-[3-(4'-ethoxy carbonyl phenyl)-2-propen]-yl-2-benzylidene adamantane,
(17) 4-[3-(4'-carboxy phenyl)-2-propen]-yl-2-benzylidene adamantane,
(18) 3-[5-(4'-methoxy carbonyl phenyl)-4-methyl-2,4-pentadien]-ylidene-2,2-dimethyl norbornane,

(19) 3-[5-(4'-carboxy phenyl)-4-methyl-2,4-pentadien]-ylidene-2,2-dimethyl norbornane,
(20) 4'-[4-ethylaminocarbonyl-3-methyl-1,3-butadien]-yl-2-benzylidene adamantane,
(21) 4'-(2-ethyl)-4-hexylaminocarbonyl-3-methyl-1,3-butadien]-yl-2-benzylidene adamantane,
(22) 4'-[(di-O-1,2,3,4-isopropylidene)-4-D-galacto pyranosyloxy-3-methyl-1,3-butadien]-yl-2-benzylidene adamantane,
(23) 4'-[4-ethoxycarbonyl-1,3-butadien]-yl-2-benzylidene adamantane,
(24) 4'-[4-carboxy-1,3-butadien]-yl benzylidene adamantane,
(25) 4'-[(1-ethoxycarbonyl-3-methylthio)-4propylaminocarbonyl-3-methyl-1,3-butadien]-yl-2-benzylidene adamantane and
(26) 3-[3-(4'-ethylaminocarbonyl phenyl)-2-propen]-ylidene-2,2-dimethyl norbornane.

Various synthesis methods can be employed to produce the compounds of formula I. These methods are as follows:

A—FIRST METHOD

This method comprises condensing a compound of formula (1) on a compound of formula (2).

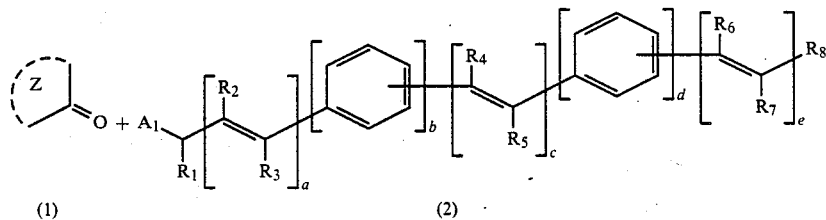

(1)    (2)

According to this method, the different radicals of the compound of formula (2) can have the meanings given above for general formula I, $R_8$ not representing

while $R_{10}$ represents hydrogen or alkyl.

$A_1$ represents either a triarylphosphonium group of the formula: $-P[X]_3 \oplus Y \ominus$, X being aryl and Y being an anion of an organic or inorganic acid, or a dialkoxyphosphinyl group of the formula

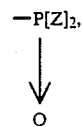

Z being an alkoxy group.

When $A_1$ represents $-P[X]_3 \oplus Y \ominus$, *the condensation is carried out in the presence of an alkali metal alcoholate, such as sodium methylate, or in the presence of an alkylene oxide optionally substituted by an alkyl group, in a solvent such as methylene chloride or dimethylformamide. The temperature of the reaction is between ambient temperature and the boiling temperature of the reaction mixture.*

When $A_1$ represents

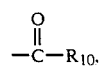

the condensation is carried out in the presence of a base and preferably in the presence of an inert organic solvent, for example, by means of sodium hydride in benzene, toluene dimethylformamide, tetrahydrofuran, dioxane or 1,2-dimethoxyethane, or also by means of an alcoholate, for example, by means of sodium methylate in methanol, at a temperature ranging between 0° C. and the boiling point of the reaction mixture. The condensation can also be carried out by using a mineral base such as KOH or NaOH, in an organic solvent such as tetrahydrofuran. There can be added to the reaction mixture a ring ether capable of complexing the metallic cation contained in the base which permits to increase its strength. This method is quite particularly appropriate for the synthesis of compounds of formula II.

B—SECOND METHOD

This method comprises condensing a compound of formula (3) on a compound of formula (4).

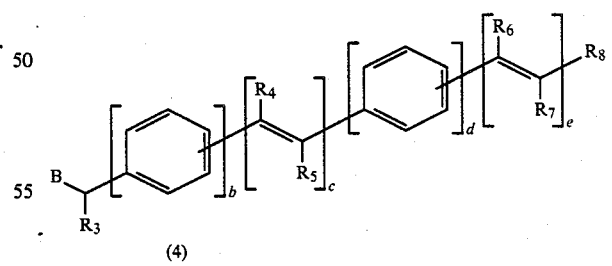

According to this method, the various radicals of the compounds of formulas (3) and (4) can have the meanings given above for general formula I, $R_8$, however, not representing

with $R_{10}$ representing hydrogen or alkyl.

In formulas (3) or (4), A or B represents an oxo group, and the other represents either a triarylphosphonium group of the formula —P[X]$_3^\oplus$Y$^\ominus$ or a dialkoxyphosphinyl group of the formula

wherein X, Y and Z have the same meanings given above for the first method.

The condensation reaction conditions are the same as those described above for the first method as a function of the meanings of A and B.

C—THIRD METHOD

This method comprises condensing a compound of general formula (5) on a compound of general formula (6).

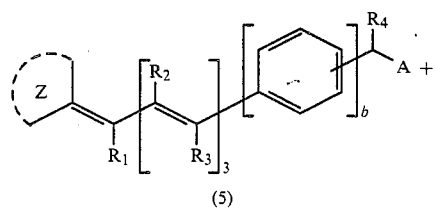

(5)

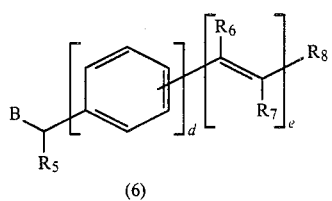

(6)

According to this method, the various radicals of the compounds of formulas (5) and (6) can have the same meanings given for general formula I, $R_8$ however not representing

with $R_{10}$ representing hydrogen or alkyl.

In one of the formulas (5) or (6) A or B represents an oxo group and the other represents either a triarylphosphonium group of the formula —P[X]$_3^\oplus$Y$^\ominus$ or a dialkoxyphosphinyl group of the formula

wherein X, Y and Z have the meanings given above.

The condensation reaction conditions are the same as those described above for the first method as a function of the meanings of A and B.

This method is quite particularly appropirate for the preparation of compounds of formulas III and IV.

The compounds obtained according to the methods described above, can undergo functional modifications of the substituent $R_8$; for example, the saponification of an ester of carboxylic acid or the reduction of the ester group of carboxylic acid into a hydroxymethyl group. The hydroxymethyl group can also be oxidized into a formyl group, or even esterified or etherified. On the other hand, a carboxyl group can be converted to a salt, an ester, an amide, an alcohol, an acetyl group or into a corresponding acid chloride. An ester group of carboxylic acid can be converted into an acetyl group. The acetyl group can be converted into a secondary alcohol group by reduction, and the secondary alcohol group can itself be alkylated or acylated. All these functional modifications can be carried out by known procedures.

The compounds of formula I are obtained as cis/trans mixtures that can be separated, by known procedures, into the cis compounds and the trans compounds or can be isomerized into entirely trans compounds.

The present invention also relates to intermediate products of synthesis of the following formula:

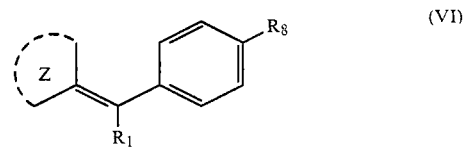

(VI)

wherein $R_1$ represents hydrogen, $R_8$ represents —CH$_2$OH or

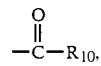

$R_{10}$ represents hydrogen, lower alkyl or —OR$_{11}$, $R_{11}$ represents hydrogen or alkyl and Z represents the cycloaliphatic residue derived from adamantane, norbornane or cyclododecane.

Representative compounds of formula VI, above, include:

(1) 2-[4'-ethoxy carbonyl] benzylidene adamantane,
(2) 2-[4'-carboxy] benzylidene adamantane,
(3) 2-[4'-formyl] benzylidene adamantane,
(4) 2-[4'-ethoxy carbonyl] benylidene norbornane,
(5) 2-[4'-formyl] benzylidene norbornane,
(6) 2-[4'-ethoxy carbonyl] benzylidene cyclododecane,
(7) 2-[4'-hydroxymethyl] benzylidene cyclododecane,
(8) 2-[4'-formyl] benzylidene cyclododecane and
(9) 2-[4'-methylcarbonyl] benzylidene adamantane.

These compounds, in addition to the fact of being intermediates, find use in the cosmetic field as an active agent or as a component in anti-solar compositions.

According to the present invention, it has been noted that the compounds of formula I are indeed particularly suitable for the treatment of dermatologic diseases linked to a keratinization disorder (differentiation-proliferation) as well as dermatologic diseases, or other with inflammatory and/or immunoallergic components, principally for the treatment of acne vulgaris, blackheads or polymorphes, acne seniles, sunlight and medicinal or professional acne, extensive and/or severe forms of psoriasis, and other keratinization disorders, and principally ichtyosis and ichtyosis-like states, Darier illness, palmoplantary keratodermies, leucoplasies and leucoplasie-like states, lichen plan, all benign or malignant dermatologic proliferations, extensive or severe; they are also active against rheumatoid psoriases. These compounds also find use in the opthamologic field, in particular, in the treatment of corneopathies and for the treatment of atopy whether cutaneous or respiratory. The present invention thus also relates to medicinal compositions containing the compounds of formula I.

The present invention consequently also relates to a medicinal composition, intended principally for the treatment of the above-mentioned diseases, characterized by the fact that they comprise, in a pharmaceutically acceptable support, at least one compound of formula I and/or one of its isomers and/or one of its salts.

It has been observed that the compounds according to the present invention exhibit good activity on a very wide range of dilution; there can be used, principally, concentrations of the active component ranging from 0.0005% to 2% by weight, based on the total weight of the composition. It is possible, however, to use higher concentrations when it is necessary for a particular therapeutic use; however, the preferred concentrations of the active principle are between 0.01 and 1% by weight, based on the total weight of the composition.

When the compounds according to the invention are used topically, they are provided, advantageously, in the form of ointments, gels, creams, pomades, powders, tinctures, solutions, suspensions, emulsions, lotions, sparys, or impregnated stamps or pads. The compounds according to the invention are mixed with non-toxic inert supports, generally liquid or pastey, which are suitable for topical treatment.

There can advantageously be employed solutions having about 0.01%–0.3% by weight of the active substance and creams having about 0.02%–0.5% by weight of active substance.

The compounds according to the invention can be used enterally. When administered orally, the compounds according to the present invention can be administered at a rate of about 2 $\mu$g up to 2 mg per day and per kilogram of body weight; an excessive posology can be manifested under the form of a hypervitaminose A recognizable wiith its symptoms. The required dosage can be administered in one or more doses. For oral administration, the appropriate forms are, for example, tablets, gelules, lozenges, syrups, suspensions, emulsion, solutions, powders, and granules; a preferred mode of administration comprises using gelules containing from 0.1 mg to about 1 mg of the active substance.

The compounds according to the invention can also be administered parenterally under the form of solutions or suspensions for perfusions or intravenous or intramusclar injections. In this case, one administers the compounds according to the invention at a rate of about 2 $\mu$g up to 2 mg per day and per kilogram of body weight. A preferred mode of administration comprises using solutions or suspensions containing from 0.1 mg to about 1 mg of the active substance per milliliter.

The pharmaceutically acceptable support can comprise water, gelatin, lactose, starch, talc, petrolatum, gum arabic, polyalkyleneglycols or magnesium stearate. The tablets, powders, lozenges, granules or gelules can contain binders, charges, or pulverulent supports. The solutions, creams, suspensions, emulsions or syrups can contain diluents, solvents, or thickeners.

In the treatment of keratinization disorders, the compounds according to the present invention, used in the medicinal compositions defined above, act by increasing the follicular epithelial production of non-adherent cells, thus dislodging and removing the content of the acne comedon. These compounds reduce the size of the sebaceous glands and partially inhibit the secretion of sebum.

The compounds according to the invention can also be administered ocularly in the form of solutions or dispersions (eye wash).

The compounds of formula I, according to the invention, also find use in the cosmetic field, in particular in capillary and body hygiene formulations, and principally in the treatment of skin tending to acne, seborrhea and loss of hair and for the regrowth of hair, as well as for the treatment of physiologically dry skin. Finally, they have a preventative and curative power against the bad effects of sunlight.

The present invention thus also relates to a new cosmetic composition, characterized by the first that it contains in a cosmetically acceptable support at least one compound of formula I and/or one of its isomers and/or one of its salts. This composition can be provided in the form of lotions, gels, creams, soaps, shampoos or the like.

The concentration of the compound of formula I in these cosmetic compositions is betweenn 0.0005 to 2 weight percent and preferably between 0.01 to 1 weight percent based on the total weight of the composition.

The cosmetic compositions according to the invention can contain inert additives or even pharmacodymanically or cosmetically active components and principally, hydrating agents such as urea, thiamorpholinone and its derivatives; antiseborrheic agents such as S-carboxymethyl cysteine, S-benzyl cysteamine, their salts and their derivatives and tioxolone or even benzoyl peroxide; antibiotics such as erythromycin and its esters, neomycin, tetracyclines or polymethylene-4,5-iosothiazoliones; agents favoring the regrowth of hair such as "Minoxidil" (2,4-diamino-6-piperidino-3-pyrimidine oxide) and its derivatives, Diazoxide (7-chloro-3-methyl-1,2,4-benzothiadiazine-1,1-dioxide) and Phenytoin (5,5-diphenyl-2,4-imidazolidinedion); steroidal or non-steroidal anti-inflammatory agents; carotenoids and principally, $\epsilon$-carotene; antipsoriasis agents such as anthralin and its derivatives, 5,8,11,14-eicosatetraynoic and 5,8,11-eicosatriynoic acids, theirs esters and their amides.

The compositions according to the invention can also contain sapidity agents, preservatives, stabilizers, humidity regulators, pH regulators, osmotic pressure regulators, emulsifiers, UV-B and UV-A filters, and antioxidants such as $\alpha$-tocopherol, butylhydroxy anisole or butylhydroxy toluene.

To better understand the invention, several non-limiting examples of the preparation of the initial reactants and compounds of the invention, as well as several examples of cosmetic and pharmaceutical compositions are given.

PREPARATION OF INITIAL REACTANTS

Example A

Preparation of 2-[4'ethoxycarbonyl]benzylidene adamantane—Compound of formula VI wherein: $R_1=H$, $R_8=-CO_2C_2H_5$ and Z is the residue derived from adamantane There are slowly added over a 30 minute period, 40 g of diethyl 4-ethoxy carbonyl benzylphosphonate to 6 g of sodium hydride in 60 cm³ of tetrahydrofuran containing 0.5 g of 1,4,7,10,13 pentaoxa cyclopentadecane. The mixture is stirred for 1 hours, and the temperature of the reaction mixture is then raised from 18° to 30° C.

Over a one-hour period there are added 20 g of 2-adamantanone in solution in 100 cm³ of tetrahydrofuran. The reaction mixture is stirred for 3 hours at ambient temperature at which point 50 cm³ of water are added. The reaction mixture is extracted with ether and the organic phase is dried on sodium sulfate. After evaporation of the solvent, the residue is purified by chromatography on silica gel (eluant: toluene).

14 g of the expected product having the following characteristics are obtained:

Melting point: 60° C. UV spectra (chloroform): $\lambda$max: 284 nm, $\epsilon$: 13100

| Elemental analysis: | C | H | O |
|---|---|---|---|
| Calculated: | 81.04 | 8.16 | 10.79 |
| Found: | 81.01 | 8.14 | 10.89 |

Example B

Preparation of 2-[4-carboxy] benzylidene adamantane — Compound of formula VI wherein $R_1$=H, $R_8$=$CO_2H$ and Z represents the residue derived from adamantane This compound is obtained by hydrolysis of the compound of Example A at reflux for 1 hour in the presence of an ethanolic solution of 2N NaOH. After cooling the solvent is evaporated. The remainder is acidified and the precipitate is washed with water.

After recrystallization in acetone, the resulting product has the following characteristics:

Melting point: 236° C. UV spectra (chloroform): $\lambda$max: 286, $\epsilon$: 17300

| Elemental analysis: | C | H | O |
|---|---|---|---|
| Calculated: | 80.56 | 7.51 | 11.92 |
| Found: | 80.36 | 7.49 | 11.87 |

Example C

Preparation of 2-[4'-formyl]benzylidene adamantane — Compound of formula VI wherein $R_1$=H, $R_8$=—CHO and Z represents the residue derived from adamantane 15 g of the compound obtained in Example A are added to 3 g of the hydride of lithium and aluminum in 200 cm³ of ether.

The reaction mixture is stirred for 1 hour at 30° C., at which point it is cooled to —30° C., 100 cm³ of ethylacetate and 200 cm³ of water are then added.

The reaction mixture is then filtered on celite. The aqueous phase is washed with ethyl acetate and the organic phase is dried on sodium sulfate. The solvent is evaporated and the residue is redissolved in 100 cm³ of ether. 30 g of manganese dioxide are added, and the reaction mixture is stirred overnight at ambient temperature.

The reaction mixture is then filtered on celite and the solvet is evaporated. Thereafter, the residue is recrystallized in ethanol.

3 g of the expected product having the following characteristics are obtained:

Melting point: 78° C. UV spectra (chloroform): $\lambda$max: 308 nm $\epsilon$: 14300

| Elemental analysis: | C | H | O |
|---|---|---|---|
| Calculated: | 85.67 | 7.98 | 6.34 |
| Found: | 85.48 | 8.01 | 6.60 |

Example D

Preparation of 2-[4'-ethoxycarbonyl]benzylidene norbornane — Compound of formula VI wherein: $R_1$=H, $R_8$=$CO_2C_2H_5$ and Z represents the residue derived from norbornane This compound is obtained according to the same method as that described in Example A, but by replacing 2-adamantanone with norcamphor.

The resulting product is purified by chromatography on silica gel (eluant: hexane/ethyl acetate, 9/1).

It has the following characteristics: UV spectra ($CHCl_3$): $\lambda$max:293 nm, $\epsilon$: 24800

Example E

Preparation of 2-[4'-formyl]benzylidene norbornane — Compound of formula VI wherein $R_1$=H, $R_8$=—CHO and Z represents the residue derived from norbornane This compound is obtained according to the same procedures as those described in Example C wherein the compound of Example A is replaced by the compound of Example D.

The resulting product is purified by chromatography on silica gel (eluant: hexane/ethyl acetate, 9/1).

Example F

Preparation of 2-[4'-ethoxy carbonyl]benzylidene cyclododecane — Compound of formula VI wherein: $R_1$=H, $R_8$=$CO_2C_2H_5$ and Z represents the residue derived from cyclododecane This compound is obtained according to the same procedures as those described in Example A, but by replacing 2-adamantanone by cyclododecane. The resulting product is purified by repeated recrystallizations in ethanol. It has the following characteristics:

Melting point: 55° C. UV spectra ($CHCl_3$): $\lambda$max: 282 nm, $\epsilon$: 15600

| Elemental analysis: | C | H | O |
|---|---|---|---|
| Calculated: | 80.49 | 9.76 | 9.76 |
| Found: | 80.38 | 9.86 | 9.75 |

Example G

Preparation of 2-[4'-hydroxymethyl]benzylidene cyclododecane — Compound of formula VI wherein: $R_1$=H, $R_8$=—$CH_2OH$ and Z represents the residue derived from cyclododecane 1 g of the hydride of aluminum and lithium is suspended in 70 cm³ of ether. To this suspension there is slowly added at about 10° C. a solution of 8 g of the compound obtained in Example F in 20 cm³ of ether. The mixture is stirred for 1 hour at ambient temperature, then there are slowly added 20 cm³ of ethyl acetate and a few cubic centimeters of water. The reaction mixture is filtered on celite, and the solvent is distilled off under reduced pressure. The residue is purified by chromatography on silica gel (eluant: hexane/ethyl acetate, 9/1). After recrystallization in hexane, 5.5 g of the expected product having the following characteristics are obtained:

Melting point: 68° C. UV spectra (CHCl$_3$): $\lambda$max: 254 nm, $\epsilon$: 14400

| Elemental analysis: | C | H | O |
|---|---|---|---|
| Calculated: | 83.92 | 10.49 | 5.59 |
| Found: | 84.11 | 10.46 | 5.84 |

Example H

Preparation of 2-[4'-formyl]benzylidene cylododecane — Compound of formula VI wherein: $R_1$=H, $R_8$=—CHO and Z represents the residue derived from cyclododecane There is stirred for 18 hours at ambient temperature a mixture of 5.4 g of the compound obtained in Example G and 11 g of manganese dioxide activated in 100 cm$^3$ of ether. The mixture is filtered on celite, and the solvent is evaporated. After recrystallization of the residue in hexane, 5 g of the expected product having the following characteristics are obtained:

Melting point: 58° C. UV spectra (CHCl$_3$): $\lambda$max: 302 nm, $\epsilon$: 16600

| Elemental analysis: | C | H | O |
|---|---|---|---|
| Calculated: | 84.51 | 9.86 | 5.63 |
| Found: | 84.55 | 9.83 | 5.84 |

Example I

Preparation of 2-[4'-methylcarbonyl]benzylidene adamantane — Compound of formula VI wherein: $R_1$=H, $R_8$=—CO—CH$_3$ and Z represents the residue derived from adamantane 20 g of the compound obtained in Example B are suspended in 150 cm$^3$ of tetrahydrofuran under argon. The suspension is cooled to about 0° C. and there are slowly added 93 cm$^3$ of 1.6M methyl lithium. The temperature is permitted to rise slowly, at which point the reaction mixture is cooled again to about 0° C. 65 cm$^3$ of chlorotrimethylsilane are slowly added. Then 35 cm$^3$ of 1N HCl are added. The reaction mixture is diluted with 150 cm$^3$ of water and then extracted with ether. The organic phase is dried and the solvent is evaporated. 19.9 g of product which is recrystallized in an ethanol-water mixture are obtained. The recrystallized product has the following characteristics:

Melting point: 72° C. UV spectra (chloroform): $\lambda$max: 298 nm, $\epsilon$: 17800

| Elemental analysis: | C | H | O |
|---|---|---|---|
| Calculated: | 85.71 | 8.27 | 6.02 |
| Found: | 85.21 | 8.30 | 6.30 |

PREPARATION OF THE COMPOUNDS OF THE PRESENT INVENTION

Example 1

Preparation of 3-[3-(4'-methoxy carbonyl phenyl)-2-propen]-ylidene-2,2-dimethyl norbornane— Compound of formula II wherein: $R_1$, $R_2$ and $R_3$=H, $R_8$=—CO$_2$CH$_3$ and Z represents the residue derived from 2,2-dimethyl norbornane A suspension of 30 g of 2,2-dimethyl-3-triphenylphosphonio-ethylidene-2,2,1-bicyclo heptane bromide in 600 cm$^3$ of anhydrous ether is cooled to −70° C.

68 cm$^3$ of a 1.6M solution of butyl lithium and 150 cm$^3$ of tetrahydrofuran are added. The temperature of the mixture slowly rises up to about 0° C., at which point the mixture is recooled to −70° C. There are then added over a twenty-minute period 10 g to 4-methoxycarbonyl benzaldehyde in solution in 50 cm$^3$ of tetrahydrofuran and 50 cm$^3$ of ether.

The temperature thereof is permitted to return slowly to ambient temperature at which point 50 cm$^3$ of diluted acetic acid are added. The organic phase is decanted, washed with bicarbonated water, then with water and subsequently dried on sodium sulfate. After evaporation of the solvent, the residue is chromatographed on silica gel (eluant: hexane/ethyl acetate, 99/1).

4 g of the expected product havign the following characteristics are obtained:

Melting point: 128° C. UV spectra (chloroform): $\lambda$max: 333 nm, $\epsilon$: 35500

| Elemental analysis: | C | H | O |
|---|---|---|---|
| Calculated: | 81.04 | 8.16 | 10.79 |
| Found: | 81.20 | 8.29 | 10.66 |

Example 2

Preparation of 3-[3(4'-carboxyphenyl)-2-propen]-ylidene-2,2-dimethyl norbornane— Compound of formula II wherein: $R_1$, $R_2$ and $R_3$=H, $R_8$=—COOH and Z represents the residue derived from 2,2-dimethyl norbornane There is heated for one hour at reflux a solution of 1.2 g of the compound obtained in Example 1 in 30 cm$^3$ of ethanol and 3 cm$^3$ of 2N NaOH.

The solvent is evaporated, and the remainder is acidified. The resulting precipitate is washed with water. On recrystallization in 20 cm$^3$ acetone, 0.5 g of the expected product having the following characteristics is obtained:

Melting point: 226° C. Uv spectra (methanol): $\lambda$max: 319 nm, $\epsilon$: 38000

| Elemental analysis: | C | H | O |
|---|---|---|---|
| Calculated: | 80.81 | 7.85 | 11.33 |
| Found: | 80.82 | 7.80 | 11.09 |

Example 3

Preparation of 4'-[4-ethoxy carbonyl-3-methyl-1,3-butadien]yl-2-benzylidene adamantane — Compound of formula III wherein: c=0, $R_1$, $R_6$, $R_7$ and $R'_7$=H, $R'_6$=—$CH_3$, $R_8$=—$CO_2C_2H_5$ and Z represents the residue derived from adamantane 3.85 g of diethyl 3-ethoxycarbonyl-2-methyl-2-propenyl phosphonate are added to a suspension of 1.5 g of crushed potash in 10 cm$^3$ of tetrahydrofuran.

After 10 minutes of contact, 3 g of the compound obtained in Example C are added. The mixture is stirred for one hour at ambient temperature and then diluted with 100 cm$^3$ of toluene. The reaction mixture is filtered on celite, and the filtrate is then evaporated.

The resulting product is recrystallized in ethanol and 3 g of the expected product having the following characteristics are recovered:

Melting point: 76° C. UV spectra (CHCl$_3$): λmax: 340 nm, ε: 35400

| Elemental analysis: | C | H | O |
|---|---|---|---|
| Calculated: | 82.83 | 8.34 | 8.82 |
| Found: | 83.04 | 8.37 | 9.05 |

Example 4

Preparation of 4'-[4-carboxy-3-methyl-1,3-butadiene]yl-2-benzylidene adamantane — Compound of formula III wherein: c=0, $R_1$, $R_6$, $R_7$ and $R'_6$=—$CH_3$, $R_8$=—$CO_2H$ and Z represents the residue derived from adamantane This compound is obtained by hdyrolysis of the compound of Example 3 in accordance with the same procedures as those described in Example 2.

After recrystallization in an acetone-hexane mixture, the resulting product has the following characteristics:

Melting point: 218° C. UV spectra (CHCl$_3$): εmax: 342 nm, λ: 36250

| Elemental analysis: | C | H | O |
|---|---|---|---|
| Calculated: | 82.59 | 7.83 | 9.56 |
| Found: | 81.84 | 7.50 | 9.36 |

Example 5

Preparation of 2-[3-(4'-methoxycarbonyl phenyl)-2-methyl-2-propen]ylidine adamantane — Compound of formula II wherein: $R_1$ and $R_3$=H, $R_2$=—$CH_3$, $R_8$=—$CO_2CH_3$ and Z represents the residue derived from adamantane This compound is obtained according to the same procedures as those described in Example A, but by replacing diethyl 4-ethoxy carbonyl benzylphosphonate by diethyl 3-(4-methoxycarbonyl phenyl)-2-methyl-2-propenyl phosphonate.

The resulting product is purified by chromatography on silica gel (eluant: hexane-ethyl acetate, 9/1). It has the following characteristics:

Melting point: 56°–58° C. UV spectra (CHCl$_3$): λmax: 310 nm, ε: 18100

| Elemental analysis: | C | H | O |
|---|---|---|---|
| Calculated: | 81.95 | 8.13 | 9.92 |
| Found: | 81.88 | 8.15 | 10.03 |

Example 6

Preparation of 2-[3-(4'-carboxy phenyl)-2-methyl-2-propen]ylidene adamantane — Compound of formula II wherein: $R_1$ and $R_3$=H, $R_2$=$CH_3$, $R_8$=—$CO_2H$ and Z represents the residue derived from adamantane This compound is obtained by hydrolysis of the compound of Example 5 according to the same procedures as those described in Example 2.

After recrystallization in acetic acid, the resulting product has the following characteristics:

Melting point: 188° C. UV spectra (CHCl$_3$): λmax: 313 nm, ε: 19400

| Elemental analysis: | C | H | O |
|---|---|---|---|
| Calculated: | 81.78 | 7.84 | 10.38 |
| Found: | 81.67 | 7.98 | 10.29 |

Example 7

Preparation of 2-[3-(4'methoxycarbonyl phenyl)-2-methyl-2-propen]ylidene norbornane — Compound of formula II wherein: $R_1$ and $R_3$=H, $R_2$=$CH_3$, $R_8$=—$CO_2CH_3$ and Z represents the residue derived from norbornane This compound is obtained according to the same procedures as those described in Example A, but by replacing diethyl 4-ethoxy carbonyl benzylphosphonate by 3-(4-methoxycarbonyl phenyl)-2-methyl-2-propenyl phosphonate and 2-adamantanone by norcamphor.

The resulting product is purified by chromatography on silica gel (eluant: hexane/ethyl acetate, 9/1).

Example 8

Preparation of 2-[3-(4'-carboxyphenyl)-2-methyl-2-propen]-ylidene norbornane — Compound of formula II wherein: $R_1$ and $R_3$=H, $R_2$=$CH_3$, $R_8$=$CO_2H$ and Z represents the residue derived from norbornane This compound is obtained by hydrolysis of the compound of Example 7 according to the same procedures as those described in Example 2.

After two recrystallizations in acetone, the expected product has the followign characteristics:

Melting point: 221° C. UV spectra (CHCl$_3$): λmax: 323 nm, ε: 23800

| Elemental analysis: | C | H | O |
|---|---|---|---|
| Calculated: | 80.56 | 7.51 | 11.92 |
| Found: | 80.47 | 7.54 | 11.87 |

Example 9

Preparation of 4'-[4-ethoxycarbonyl-3-methyl-1,3-butadien]yl-2-benzylidene norbornane — Compound of formula III wherein: c=0, $R_1$, $R_6$, $R_7$ and $R'_7$=H, $R'_6$=CH$_3$, $R_8$=—CO$_2$C$_2$H$_5$ and Z represents the residue derived from norbornane This compound is obtained according to the same procedures as those described in Example 3, but by replacing the compound of Example C by the compound of Example E.

After recrystallization in ethanol, the resulting compound has the following characteristics:

Melting point: 58° C. UV spectra (CHCld$_3$): λmax: 348 nm, ε: 28300

| Elemental analysis: | C | H | O |
|---|---|---|---|
| Calculated: | 81.95 | 8.13 | 9.92 |
| Found: | 82.04 | 8.15 | 9.97 |

Example 10

Preparation of 4'-[4-carboxy-3-methyl-1,3-butadien]yl-2-benzylidenne norbornane — Compound of formula III wherein: c=0, $R_1$, $R_6$, $R_7$ and $R'_7$=H, $R'_6$=CH$_3$, $R_8$=—CO$_2$H and Z represents the residue derived form norbornane This compound is obtained by hydrolysis of the compound of Example 9 according to the same procedures as those described in Example 2.

After recrystallization in acetone, the resulting compound has the following characteristics:

Melting point: 225° C. UV spectra (CH$_3$OH): λmax: 340 nm, ε: 42200

| Elemental analysis: | C | H | O |
|---|---|---|---|
| Calculated: | 81.60 | 7.53 | 10.87 |
| Found: | 81.67 | 7.57 | 10.66 |

Example 11

Preparation of 2-[3-(4'-N-ethylamino carbonyl phenyl)-2-methyl-2-propen]ylidene adamantane — Compound of formula II wherein: $R_1$ and $R_3$=H, $R_2$=CH$_3$, $R_8$=—CONHC$_2$H$_5$ and Z represents the residue derived from adamantane 0.6 g of the compound obtained in Example 6 and 0.31 g of carbonyl diimidazole are suspended in 10 cm$^3$ of dimethylformamide. The suspension is heated at 70° C. for 2 hours.

Thereafter, the suspension is cooled to 0° C. and 1 cm$^3$ of ethylamine is added. The mixture is stirred for 2 hours, diluted with water and then extracted with ether. After evaporation of the ether, the oily residue is recrystallized in 96° alcohol. 0.2 g of product having the following characteristics is obtained:

Melting Point: 94°–96° C. UV spectra (chloroform): λmax: 305 nm, ε: 18700

| Elemental analysis: | C | H | N | O |
|---|---|---|---|---|
| Calculated: | 82.34 | 8.71 | 4.18 | 4.77 |
| Found: | 82.26 | 8.96 | 4.11 | 5.03 |

Example 12

Preparation of 4'-[4-ethoxycarbonyl-3-methyl-1,3-butadien]yl benzylidene cyclododecane — Compound of formula III wherein: c=0, $R_1$, $R_6$, $R_7$ and $R'_7$=H, $R'_6$=CH$_3$, $R_8$=—CO$_2$C$_2$H$_5$ and Z represents the residue derived from cyclododecane There are slowly added under argon, 4 cm$^3$ of 2.5M butyl lithium with a mixture of 20 cm$^3$ of tetrahydrofuran and 20 cm$^3$ of hexamethyl phosphoramide at 0° C. The mixture is cooled to −30° C. and there are slowly introduced 1.7 cm$^3$ of diisopropylamine. The resulting mixture is cooled to −60° C. and 2.7 g of diethyl 3-ethoxycarbonyl-2-methyl-2-propenyl phosphonate in 10 cm$^3$ of tetrahydrofuran are slowly added. The reaction mixture is then stirred at this temperature for 45 minutes, at which point a solution of 2.9 g of the compound obtained in Example H in 20 cm$^3$ of tetrahydrofuran is slowly added.

The mixture is stirred for 2 hours at −10° C. Thereafter, a saturated solution of ammonium chloride is added. The reaction mixture is extracted with ether; the etherified phase is washed with water and dried on sodium sulfate. The solvent is distilled off under reduced pressure.

After recrystallization in hexane, 2.4 g of the expected product having the following characteristics are obtained:

Melting point: 80° C. UV spectra (chloroform) λmax: 326 nm, ε: 33900

| Elemental analysis: | C | H | O |
|---|---|---|---|
| Calculated: | 82.23 | 9.64 | 8.12 |
| Found: | 82.44 | 9.70 | 8.28 |

Example 13

Preparation of 4'-[4-carboxy-3-methyl-1,3-butadien]yl benzylidene cyclododecane — Compound of formula III wherein: c=0, $R_1$, $R_6$, $R_7$ and $R'_7$=H, $R'_6$=CH$_3$, $R_8$=—CO$_2$H and Z represents the residue derived from cyclododecane This compound is obtained by hydrolysis of the compound of Example 12, according to the same procedures as those described in Example 2.

After recrystallization in acetic acid, the resulting product has the following characteristics:

Melting point: >260° C. UV spectra MDSO+MeOH: max: λ335 nm

| Elemental analysis: | C | H | O |
|---|---|---|---|
| Calculated: | 79.38 | 9.13 | 11.49 |
| Found: | 79.20 | 8.94 | 11.86 |

Example 14

Preparation of 4'-[3-cyano-2propen]yl-2-benzylidene adamantane having the formula

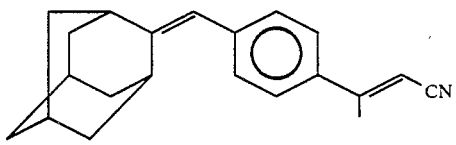

10 g of the product obtained in Example I are suspended in 40 cm³ of tetrahydrofuran. There are initially added 6.72 g of diethyl cycanomethylphosphonate, followed by the addition of 5 g of crushed potash. The mixture is stirred for 1 hour, diluted with toluene, and then filtered on silica gel+celite. The solvent is distilled off under reduced pressure. After recrystallization in ethanol, 6.7 g of pale yellow crystals having the following characteristics are obtained:

Melting point: 96° C. UV spectra (chloroform): λmax: 310 nm, ε: 23275

| Elemental analysis: | C | H | O |
|---|---|---|---|
| Calculated: | 87.76 | 7.36 | 4.87 |
| Found: | 87.69 | 7.38 | 4.91 |

Example 15

Preparation of 4'-(3-formyl-2-propen)yl-2-benzylidene adamantane having the formula

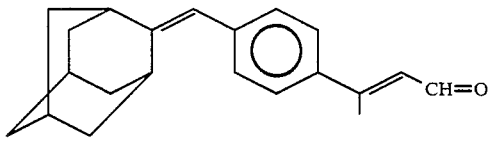

6 g of the compound obtained in Example 14 are suspended in 100 cm³ of anhydrous toluene. The suspension is cooled to −70° C. and 26 cm³ of diisobutyl aluminum hydride in a 1M solution in hexane are added. The temperature is permitted to return to 0° C., and the mixture is stirred for 30 minutes at this temperature. Diluted HCl is slowly added and the mixture is filtered on celite. The toluene phase is decanted, washed with water, dried and evaporated to dryness,. 5.1 g of yellow product are obtained.

Example 16

Preparation of 4'-[6-ethoxycarbonyl-1,5-dimethyl-1,3,5-hexatrien]yl-2-benzylidene adamantane — Compound of formula III wherein: $c=1$, $R_1=R_5=R_6=R_7=R'_7=H$, $R_4=R'_6=CH_3$, $R_8=CO_2C_2H_5$ and Z represents the residue derived from adamantane There are added together under argon at 0° C., 8 cm³ of 2.5M butyl lithium, 50 cm³ of tetrahydrofuran and 50 cm³ of hexamethylphosphoramide. The mixture is cooled to about −30° C. and 2.8 cm³ of diisopropylamine are rapidly introduced. This mixture is cooled to −60° C. and 4.6 of diethyl 3-ethoxycarbonyl-2-methyl-2-propenyl phosphonate in 20cm³ of tetrahydrofuran are added. The mixture is stirred for 30 minutes, at which point 5 g of the compound obtained in Example 15 in solution in 30 cm³ of tetrahydrofuran are added. The temperature or the mixture rises to about 0° C. and is stirred for 30 minutes. A saturated solution of ammonium chloride is added, and the organic phase is extracted with either, washed with water and dried on anhydrous sodium sulfate.

After evaporation of the solvent under reduced pressure and recrystallization in ethanol, 4.9 g of the expected product having the following characteristics are obtained:

Melting point: 108° C. UV spectra (CHCl₃): λ max: 360 nm, ε:45200

| Elemental analysis: | C | H | O |
|---|---|---|---|
| Calculated: | 83.54 | 8.51 | 7.95 |
| Found: | 83.35 | 8.41 | 8.06 |

Example 17

Preparation of 4'-[6-carboxy-1,5,-diemthyl-1,3,5-hexatrien]yl-2-benzylidene adamantane—Compound of formula III wherein: $c=1$, $R_1=R_5=R_6=R_7=R'_7=H$, $R_4=R'_6=CH_3$, $R_8=-CO_2H$ and Z represents the residue derived from adamantane This compound is obtained by hydrolysis of the compound of Example 16 according to the same procedures as those described in Example 2.

After recrystallization in methanol, the expected product has the following characteristics:

Melting point: 207° C. UV spectra (MeOH): λ max: 347 nm, ε: 42770

| Elemental analysis: | C | H | O |
|---|---|---|---|
| Calculated: | 83.42 | 8.02 | 8.56 |
| Found: | 83.30 | 7.80 | 8.70 |

Example 18

Preparation of 3-[5-(4'-methoxycarbonyl phenyl)-4-methyl-2,4-pentadien]ylidene-2,2-dimethyl norbornane —Compound of formula V wherein: $R_1=R_2=R_3=R'_3=H$, $R'_2=CH_3$, $R_8=-CO_2CH_3$ and Z represents the residue derived from 2,2-dimethyl norbornane This compound is obtained according to the same procedures as those described in Example 1, but by replacing the 4-methoxy carbonyl benzaldehyde by 3-(4-methoxycarbonyl phenyl)-2-methyl-2-propenal.

The product is purified by recrystallization in hexane and possesses the following characteristics:

Melting point: 94° C. UV spectra (chloroform): λ max: 348 nm, ε: 34400

| Elemental analysis: | C | H | O |
|---|---|---|---|
| Calculated: | 82.10 | 8.38 | 9.51 |
| Found: | 82.21 | 8.41 | 9.75 |

Example 19

Preparation of 3-[5-(4'-carboxy phenyl)-4-methyl-2,4-pentadien]ylidene-2,2-dimethyl norborane—Compound of furmula V wherein: $R_1=R_2=R_3=R'_3=H, R'_2=CH_3$, $R_8=-CO_2H_3$ and Z represents the residue derived from 2,2-dimethyl norbornane This compound is obtained by hydrolysis of the compound of Example 18 according to the same procedures as those described in Example 2. After recrystallization in acetone, the resulting product has the following characteristics:

Melting point: 228° C. UV spectra (ethanol): λ max: 344 nm, ε: 38900

| Elemental analysis: | C | H | O |
|---|---|---|---|
| Calculated: | 81.94 | 8.12 | 9.92 |
| Found: | 81.88 | 8.15 | 9.77 |

Example 20

Preparation of 4'-[4-ethylaminocarbonyl-3-methyl-1,3-butadien]yl-2-benzylidene adamantane—Compound of formula III wherein: $c=0$, $R_1$, $R_6$, $R_7$ and $R'_7=H$, $R'_6=CH3$, $R_8=CONHC_2H_5$ and Z represents the residue derived from adamantane There is stirred for 2 hours at ambient temperature a mixture of 3.34 g of the compound obtained in Example 4 1.78 g of carbonyldiimidazole in 50 cm³ of tetrahydrofuran. 2 cm³ of ethylamine are added, and the mixture is stirred for 4 hours at ambient temperature. After dilution with water the reaction mixture is extracted with ether. The organic phase is washed with water, then dried on sodium sulfate. After distillation of the solvent under reduced pressure, the residue is recrystallized in ethanol. 2.3 g of white crystals having the following characteristics are obtained:

Melting point: 120° C. UV spectra (methanol): λ max: 329 nm, ε: 42200

| Elemental analysis: | C | H | N | O |
|---|---|---|---|---|
| Calculated: | 81.74 | 8.63 | 3.81 | 5.80 |
| Found: | 81.74 | 8.71 | 3.76 | 5.89 |

Example 21

Preparation of 4'-[2-ethyl-4-hexylaminocarbonyl-3-methyl-1,3-butadien]yl-2-benzylidene adamantane—Compound of formula III wherein: $c=0$, $R_1$, $R_6$, $R_7$ and $R'_7=H$, $R'_6=CH_3$,

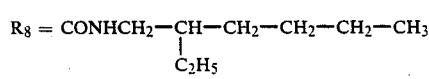

and Z represents the residue derived from adamantane

This compound is obtained according to the same procedures as those described in Example 20 in which the ethylamine is replaced by 2-ethyl hexylamine. After recrystallization in a mixture of ethanol and water, the expected product in the form of pale yellow crystals having the following characteristics is obtained:

Melting point: 102° C. UV spectra (chloroform): λ max: 334 nm, ε: 3800

| Elemental analysis: | C | H | N | O |
|---|---|---|---|---|
| Calculated: | 83.54 | 9.72 | 3.14 | 3.59 |
| Found: | 83.46 | 9.81 | 3.21 | 3.98 |

Example 22

Preparation of 4'-[4-(di-0-1,2,3,4-isopropylidene)D-galactopyranosyloxy-3-methyl-1,3-butadien]yl-2-benzylidene adamantane—Compound of formula III wherein: $c=0$, $R_1$, $R_6$, $R_7$ and $R'_7=H$, $R'_6=CH_3$,

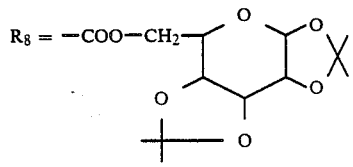

and Z represents the residue derived from adamantane

There are stirred for 30 minutes at ambient temperature, 1.5 g of the compound obtained in Example 4 and 0.87 g of carbonyldiimidazole in 50 cm³ of dichloromethane. The dichloromethane is distilled off, and a solution of 1.4 g of 1,2,3,4-di-0-isopropylidene-D-galacto-pipanose in 20 cm³ of tetrahydrofuran containing 0.28 g of sodium hydride is added. The mixture is stirred for one hour at ambient temperature and then diluted with 50 cm³ of ethyl acetate. The organic phase is washed with a saturated solution of ammonium chloride, then with water. After drying on sodium sulfate and distillation of the solvent under reduced pressure, 1 g of the expected product having the following characteristics is obtained:

Melting point: 78° C. UV spectra (chloroform): λ max 342 nm, ε: 37800

| Elemental analysis: | C | H | O |
|---|---|---|---|
| Calculated: | 72.89 | 7.69 | 19.42 |
| Found: | 73.01 | 7.68 | 19.24 |

Example 23

Preparation of 4'-[4-ethoxycarbonyl-1,3-butadien]yl-2-benzylidene adamantane—Compound of formula III wherein: $c=0$, $R_1$, $R_6$, $R'_6$, $R_7$ and $R'_7=H$, $R_8=-COOC_2H_5$ and Z represents the residue derived from adamantane There is cooled to −30° C. a solution of 4 cm³ of diisopropylamine in 20 cm³ of tetrahydrofuran. 35 cm³ of a 1.6M solution of butyl lithium in hexane and 7 cm³ of hexamethylphosphoramide are then added.

This mixture is cooled to −60° C. and 10.8 g of triethyl 4-phosphono crotonate are added. The resulting mixture is stirred for 30 minutes at this temperature, then a solution of 9 g of the compound obtained in Example C in 40 cm³ of tetrahydrofuran is added. The temperature of the mixture rises slowly to about 0° C.

After 1 hour 30 minutes of reaction, the reaction mixture is poured onto a saturated solution of ammonium chloride and is then extracted with ether. The organic phase is washed with water, then dried on sodium sulfate. After evporation of the solvent and recrystallization in hexane, 6 g of the expected product in the form of pale yellow crystals having the following characteristics are obtained:

Melting point: 80° C. UV spectra (chloroform): $\lambda$ max: 334 nm, $\epsilon$: 39000

| Elemental analysis: | C | H | O |
|---|---|---|---|
| Calculated: | 82.71 | 8.09 | 9.18 |
| Found: | 82.70 | 8.14 | 9.12 |

Example 24

Preparation of 4'-[4-carboxy-1,3-butadien]yl benzylidene adamantane—Compound of formula III wherein: c=0, $R_1$, $R_6$, $R'_6$, $R_7$ and $R'_7$=H, $R_8$=COOH and Z represents the residue of adamantane This compound is obtained by hydrolysis of the compound of Example 23, according to the same procedures as those described in Example 2.

The resulting product has the following characteristics:

Melting point: 240° C. UV spectra (DSMO+Methanol): $\lambda$ max: 335 nm, $\epsilon$: 39000

| Elemental analysis: | C | H | O |
|---|---|---|---|
| Calculated: | 82.46 | 7.54 | 9.98 |
| Found: | 82.51 | 7.43 | 10.03 |

Example 25

Preparation of 4'-[1-ethoxycarbonyl-3-methylthio-4-propylaminocarbonyl-3-methyl-1,3-butadien]yl-2-benzylidene adamantane—Compound of formula III wherein: c=0, $R_1$, $R_6$, $R_7$ and $R'_7$=H, $R'_6$=CH$_3$, $$R_8 = -CONH-\underset{CO_2C_2H_5}{CH}-(CH_2)_2-S-CH_3$$

and Z represents the residue derived from adamantane.

At 0° C., 0.65 cm$^3$ of ethyl chloroformiate is added to a solution of 2 g of the compound obtained in Example 4 in 50 cm$^3$ of tetrahydrofuran containing 2.6 cm$^3$ of triethylamine. The mixture is stirred for 15 minutes, and the triethylamine hydrochloride is filtered off. A solution of 2 g of the hydrochloride of the ethylester of L-methionine in 30 cm$^3$ of tetrahydrofuran containing 1.8 cm$^3$ of triethylamin is prepared. This solution is stirred for 15 minutes at ambient temperature, and then the triethylamine hydrochloride is filtered off. This solution is added to the preceding solution maintained at 0° C. and the resulting mixture is stirred for two hours at 0° C. and then for 24 hours at ambient temperature. The reaction mixture is poured into water and extracted with ethyl acetate. The organic phase is washed with water, then dried on sodium sulfate. The solvent is distilled under reduced pressure. After recrystallization, the expected product which has the following characteristics is obtained:

Melting point: 98° C. UV spectra (CH$_2$Cl$_2$): $\lambda$ max: 336 nm, $\epsilon$: 40200

| Elemental analysis: | C | H | N | O | S |
|---|---|---|---|---|---|
| Calculated: | 72.98 | 7.96 | 9.72 | 2.83 | 6.49 |
| Found: | 79.95 | 7.90 | 9.81 | 2.90 | 6.54 |

Example 26

Preparation of 3-[3-(4'-ethylamino carbonyl phenyl)-2-propen]ylidene-2,2-dimethyl norbornane—Compound of formula II wherein $R_1$, $R_2$ and $R_3$=H, $R_8$=—CONHC$_2$H$_5$ and Z represents the residue derived from 2,2-dimethyl norbornane.

There is heated for 15 minutes at 30° C. a mixture of 1.5 g of the compound obtained in Example 2 and 1 g of carbonyldiimidazole in 25 cm$^3$ of dichloromethane. The solvent is evaporated and 25 cm$^3$ of tetrahydrofuran are added to the residue. Then 1 cm$^3$ of ethylamine is added, and the mixture is stirred for 15 minutes at ambient temperature. The solvent is evaporated and the residue is redissolved in ethyl acetate. The organic phase after washing with water is dried on sodium sulfate, then evaporated. After crystallization of the residue in ethanol, 1.5 g of the expected product in the form of white crystals having the following characteristics are obtained:

Melting point: 136° C. UV spectra (CH$_2$Cl$_2$): $\lambda$ max: 326 nm, $\epsilon$: 36800

| Elemental analysis: | C | H | N | O |
|---|---|---|---|---|
| Calculated: | 81.51 | 8.79 | 4.53 | 5.17 |
| Found: | 81.60 | 8.74 | 4.61 | 5.01 |

EXAMPLES OF COMPOSITIONS

Example I

A gel is produced by preparing the following formulation:

| Compound of Example 2 | 0.05 g |
|---|---|
| Erythromycin base | 4.000 g |
| Butylhydroxytoluene | 0.050 g |
| Hydroxypropyl cellulose, sold under the tradename "KLUCEL HF" by Hercules | 2.000 g |
| Ethanol (95°) sufficient amount for | 100.000 g |

This gel is applied to skin with dermatosis or to an acne skin, 1 to 3 times each day.

Example II

The following formulation intended packaging in a gelule is prepared:

| Compound of Example 1 | 0.06 g |
|---|---|
| Cornstarch | 0.060 g |
| Lactose, sufficient amount for | 0.3000 g |

The gelules employed are made of gelatin, titanium oxide and a preservative. The gelules are administered to an adult individual at a rate of 1 to 3 gelules per day in the treatment of psoriasis.

Example III

An antiseborrheic lotion is prepared by admixing the following components:

| | |
|---|---|
| Compound of Example 6 | 0.03 g |
| Propylene glycol | 5.000 g |
| Butylhydroxy toluene | 0.100 g |
| Ethanol (95°), sufficient amount for | 100.000 g |

This lotion is applied twice each day on a scalp exhibiting seborrhea.

Example IV

A sunscreen cosmetic composition is prepared by admixing the following components:

| | |
|---|---|
| Compound of Example 10 | 1 g |
| Benzylidene camphor | 4 g |
| Triglycerides of fatty acids | 31 g |
| Glycerol monsterate | 6 g |
| Stearic acid | 2 g |
| Cetyl alcohol | 1.2 g |
| Lanolin | 4.0 g |
| Preservatives | 0.3 g |
| Propanediol | 2.0 g |
| Triethanolamine | 0.5 g |
| Perfume | 0.4 g |
| Demineralized water, sufficient amount for | 100.0 g |

V

A gel for topical application is prepared by admixing the following components:

| | |
|---|---|
| Compound of Example 4 | 0.05 g |
| Ethanol | 43.00 g |
| α-tocopherol | 0.05 g |
| Carbopol 941 | 0.50 g |
| Triethanolamine (20% aqueous solution) | 3.80 g |
| Water | 9.30 g |
| Propylene glycol, sufficient amount for | 100.00 g |

Example VI

A non-soluble tablet weighing 0.5 g is prepared by admixing the following components:

| | |
|---|---|
| Compound of Example 3 | 0.025 g |
| Lactose | 0.082 g |
| Stearic acid | 0.003 g |
| Purified talc | 0.015 g |
| Sweetening agent, sufficient amount | |
| Coloring agent, sufficient amount | |
| Rice starch, sufficient amount for | 0.500 g |

Example VII

A 20% solution is prepared by admixing the following components:

| | |
|---|---|
| Compound of Example 20 | 0.2 g |
| Polyethylene glycol (molecular mass = 400) | 80.0 g |
| Ethanol (95°) sufficient amount for | 100.0 g |

This solution is applied to acne skin 1 to 3 times each day, and a significant improvement is noted within 6 to 12 weeks depending on the seriousness of the acne being treated.

Example VIII

An anti-seborrhea cream is produced by admixing the following components:

| | |
|---|---|
| Polyoxyethylene stearate (40 moles of ethylene oxide) sold under the tradename Myrj 52 by Atlas | 4 g |
| Mixture of lauric esters of sorbitol and polyoxyethylene sorbitan (20 moles of ethylene oxide) sold under the tradename Tween 20 by Atlas | 1.8 g |
| Mixture of glycerol mono- and distearate sold under the name GELEOL by Gatte Fosse | 4.2 g |
| Propylene glycol | 10.0 g |
| Butylhydroxy anisole | 0.01 g |
| Butylhydroxy toluene | 0.02 g |
| Cetyl-stearyl alcohol | 6.2 g |
| Preservative, sufficient amount | |
| Perhydrosqualene | 18.0 g |
| Mixture of caprylic and capric triglycerides sold under the name Miglyol 812 by Dynamit Nobel | 4 g |
| S-carboxymethyl cysteine | 3 g |
| Triethanolamine, 99% | 2.5 g |
| Compound of Example 26 | 0.02 g |
| Water, sufficient amount for | 100.00 g |

Example IX

An antiseborrhea cream is prepared by admixing the following components:

| | |
|---|---|
| Polyoxyethylene stearate (40 moles of ethylene oxide), sold under the trade name Myrj 52 by Atlas | 4 g |
| Mixture of lauric esters of sorbitol and polyoxyethylene sorbitan (20 moles of ethylene oxide, sold under the tradename Tween 20 by Atlas | 1.8 g |
| Mixture of glycerol mono-and distearate, sold under the tradename GELEOL by Gatte Fosse | 4.2 g |
| Propylene glycol | 10.0 g |
| Butylhydroxy anisole | 0.01 g |
| Butylhydroxy toluene | 0.02 g |
| Cetyl-stearyl alcohol | 6.2 g |
| Preservative, sufficient amount | |
| Perhydrosqualene | 18 g |
| Mixture of caprylic and capric triglycerides, sold under the tradename Miglyol 812 by Dynamit Nobel | 4 g |
| 5-amino-5-carboxy-3-thia pentanoate of 2-benzylthio ethylammonium | 3 g |
| Compound of Example 26 | 0.02 g |
| Water, sufficient amount for | 100 g |

Example X

An anti-acne cream is prepared by admixing the following components:

| | |
|---|---|
| Mixture of glycerol stearates and polyethylene glycol (75 moles) sold under the tradename Gelot 64 by Gatte Fosse | 15 g |
| Noyau oil polyoxyethylenated with 6 moles of ethylene oxide sold under the tradename Labrafil M 2130 CS by Gatte Fosse | 8 g |
| Perhydrosqualene | 10 g |
| Dye, sufficient amount | |

| -continued | |
|---|---|
| Preservatives, sufficient amount | |
| Perfume, sufficient amount | |
| Tioxolone | 0.4 g |
| Polyethylene glycol 400 | 8 g |
| Purified water | 58.5 g |
| Disodium salt of ethylene diamine tetracetic acid | 0.05 g |
| Compound of Example 4 | 0.05 g |

In this Example, the compound of Example 4 can be replaced by the same amount of the compound of Example 2.

Example XI

A capillary lotion for use in the treatment of falling hair and for use in the promotion of hair growth is prepared by admixing the following components:

| Propylene glycol | 20 g |
|---|---|
| Ethanol | 34.92 g |
| Polyethylene glycol 400 | 40 g |
| Water | 4 g |
| Butylhydroxy anisole | 0.01 g |
| Butylhydroxy toluene | 0.02 g |
| Compound of Example 4 | 0.05 g |
| Minoxidil | 1 g |

Example XII

A lotion for use in the promotion of hair growth is prepared by admixing the following components:

| Propylene glycol | 13.96 g |
|---|---|
| Polyethylene glycol 300 | 40 g |
| Polyethylene glycol 1500 | 32 g |
| Isopropanol | 12 g |
| Butylhydroxy anisole | 0.01 g |
| Butylhydroxy toluene | 0.02 g |
| Compound of Example 20 | 0.05 g |
| Minoxidil | 2 g |

Example XIII

An anti-acne kit comprises 2 parts, as follows.
Part A: A gel formulation is prepared by admixing the following components:

| Ethyl alcohol | 48.4 g |
|---|---|
| Propylene glycol | 50 g |
| Carbopol 940 | 1 g |
| Diisopropylamine, 99% | 0.3 g |
| Butylhydroxy anisole | 0.05 g |
| Butylhydroxy toluene | 0.05 g |
| Tocopherol | 0.1 g |
| Compound of Example 20 | 0.1 g |

In Part A, the compound of Example 20 can be replaced by the same amount of the compound of Example 2.
Part B A gel formulation is prepared by admixing the following components:

| Ethyl alcohol | 5 g |
|---|---|
| Propylene glycol | 5 g |
| Disodium salt of EDTA | 0.05 g |
| Carbopol 940 | 1 g |
| Triethanoloamine, 99% | 1 g |
| Sodium lauryl sulfate | 0.1 g |
| Purified water | 75.05 g |

| -continued | |
|---|---|
| Benzoyl peroxide, hydrated to 25% | 12.8 g |

A mixture of the two gels is made for use, weight for weight, at the time of use.

What is claimed is:

1. An unsaturated cycloaliphatic derivative having the formula:

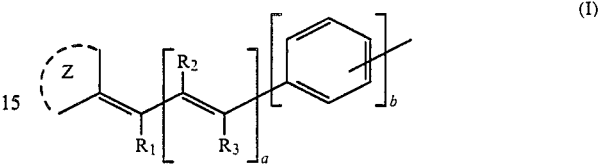

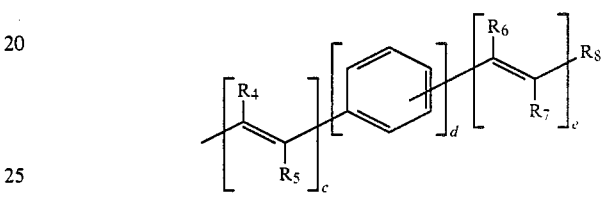

wherein $R_1$ to $R_7$, each independently, represent hydrogen or lower alkyl, $R_8$ represents $-C\equiv N$, an oxazolinyl radical or a radical corresponding to one of the following formulas:
(i) $-CH_2OR_9$ and

wherein $R_9$ represents hydrogen, lower alkyl, cyclopentyl, cyclohexyl, monohydroxyalkyl, polyhydroxyalkyl, or a tetrahydropyrannyl radical and $R_{10}$ represents hydrogen, lower alkyl, $-OR_{11}$ or

wherein r' and r'', each independently, represent hydrogen, linear or branched alkyl, monohydroxyalkyl, polyhydroxyalkyl, alkenyl, cyclopentyl, cyclohexyl, phenyl, phenyl substituted by halogen, hydroxy or lower alkoxy, benzyl, phenthyl, benzyl substituted by hydroxy or alkoxy or phenethyl substituted by hydroxy or alkoxy, or r' and r'' taken together with the nitrogen atom to which they are attached form a heterocycle selected from the group consisting of piperidino, piperazino, morpholino, pyrrolidino and 4-(2-hydroxyethyl) piperazino, or r' represents hydrogen and r'' represents the residue of methionine or glucosamine, $R_{11}$ represents hydrogen, alkyl, monohyroxy lower alkyl, polyhydroxy lower alkyl, or the residue of a sugar selected from glucose, mannitol, erythritol or galactose, Z represents a cycloaliphatic residue selected from the group consisting of norbornane, 2,2-dimethyl norborane, adamantane and cyclododecane, a and e represent 0, 1 or 2, and b, c and d represent 0 or 1, it being understood that:

a+c+e≧1 and that b and d do not represent 0 simultaneously, and the geometric and optical isomers of the said compounds of formula I, as well as their salts.

2. The derivative of claim 1 wherein $R_{11}$ represents an alkyl radical having 1-18 carbon atoms.

3. The derivative of claim 2 wherein the alkyl radical having 1-18 carbon atoms is methyl, ethyl, propyl, 2-ethyl hexyl, octyl, dodecyl, hexadecyl or octadecyl.

4. The derivative of claim 1 wherein r' and r" represent alkenyl having 3-6 carbon atoms.

5. The derivative of claim 4 wherein the alkenyl having 3-6 carbon atoms is propenyl, butenyl or isopentenyl.

6. The derivative of claim 1 wherein $R_{11}$ represents monohydroxy lower alkyl having 2-3 carbon atoms.

7. The derivative of claim 6 wherein the monohydroxy lower alkyl having 2-3 carbon atoms is 2-hydroxyethyl or 2-hydroxypropyl.

8. The derivative of claim 1 wherein $R_{11}$ represents a polyhydroxyalkyl having 3-6 carbon atoms and 2-5 hydroxyl groups.

9. The derivative of claim 8 wherein the polyhydroxyalkyl having 3-6 carbon atoms and 2-5 hdroxyl groups is 2,3-dihydroxypropyl, 2,3,4-trihydroxybutyl, 2,3,4,5-tetrahydroxypentyl or the residue of pentaerythritol.

10. The derivative of claim 1 having the formula:

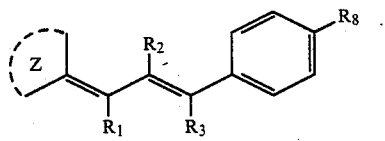

wherein $R_1$ and $R_3$ represent hydrogen, $R_2$ represents hydrogen or lower alkyl, $R_8$ represents

$R_{10}$ represent —$OR_{11}$ or

$R_{11}$ represents hydrogen, alkyl or hydroxy lower alkyl, r' and r" each independently represent hydrogen or lower alkyl, and Z represents a cycloaliphatic residue of norbornane, 2,2-dimethyl norbornane or adamantane.

11. The derivative of claim 1 having the formula:

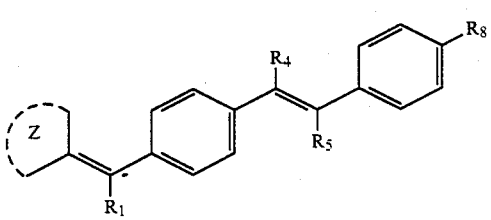

wherein $R_1$ and $R_5$ represent hydrogen, $R_4$ represents lower alkyl, $R_8$ represents

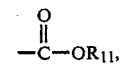

$R_{11}$ represents hydrogen, alkyl or hydroxy lower alkyl, and

Z represents a cycloaliphatic residue of admanatane.

12. The derivative of claim 1 having the formula:

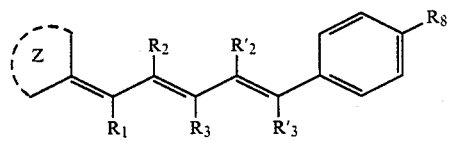

wherein $R_1$, $R_2$, $R_3$ and $R'_3$ represent hydrogen, $R'_2$ represents lower alkyl, $R_8$ represents

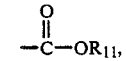

$R_{11}$ represents hydrogen, alkyl or hydroxy lower alkyl, and

Z represents a cycloaliphatic residue of 2,2-dimethyl norbornane.

13. A compound having the formula:

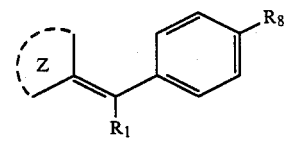

wherein $R_1$ represents hydrogen, $R_8$ represents —$CH_2OH$ or

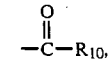

$R_{10}$ represents hydrogen, lower alkyl or —$OR_{11}$, $R_{11}$ represents hydrogen or alkyl and Z represents the cycloaliphatic residue of adamantane, norbornane or cyclododecane.

14. 3-[3(4'-carboxyphenyl)-2-propen]-ylidene-2,2-dimethyl norbornane.

15. The unsaturated cycloaliphatic derivative of claim 1 wherein r' represents hydrogen and r" represents the residue of methionine.

16. The derivative of claim 1 having the formula

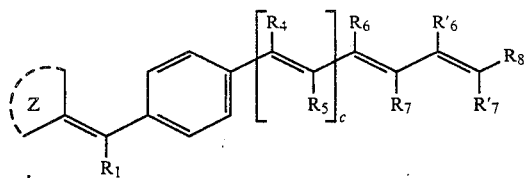

wherein
$R_1$, $R_5$, $R_6$, $R_7$ and $R'_7$ represent hydrogen,
$R_4$ represents lower alkyl,
$R'_6$ represents hydrogen or lower alkyl,
$R_8$ represents

$R_{10}$ represents $-OR_{11}$ or

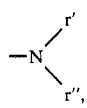

$R_{11}$ represents hydrogen, alkyl, hydroxy lower alkyl or the residue of a sugar selected from glucose, mannitol, erythritol or galactose,
r' represents hydrogen and r" represents lower alkyl or the residue of methionine,
Z represents a cycloaliphatic residue of norbornane, adamantane or cyclododecane, and
c is 0 or 1.

17. The derivative of claim 1 selected from the group consisting of:
3-[3-(4'-methoxy carbonyl phenyl)-2-propen]-ylidene-2,2-dimethyl norboranane,
3-[3-(4'-carboxy phenyl)-2-propen]-ylidene-2,2-dimethyl norbornane.
2-[3-(4'-methoxy carbonyl phenyl)-2-methyl-2-propen]-ylidene adamantane,
2-[3-(4'-carboxy phenyl)-2-methyl-2-propen]-ylidene adamantane.
2-[3-(4'-methoxy carbonyl phenyl)-2-methyl-2-propen]-ylidene norbornane,
2-[3-(4'-carboxyl phenyl)-2-methyl-2-propen]-ylidene norbornane,
4'-[4-ethoxycarbonyl-3-methyl-1,3-butadien]yl-2-benzylidene adamantane,
4'-[4-carboxy-3-methyl-1,3-butadien]yl-2-benzylidene adamantane,
4'-[4-ethoxycarbonyl-3-methyl-1,3 butadien]-yl-2-benzylidene norbornane,
4'-[4-carboxy-3-methyl-1,3-butadien]-yl-2-benzylidene norbornane, 2-[3-(4'-N-ethylamino carbonyl phenyl)-2-methyl-2-propen]-ylidene adamantane,
4'-[4-ethoxy carbonyl-3-methyl-1,3-butadien]-yl benzylidene cyclododecane,
4'-[4-carboxy-3-methyl-1,3-butadien]-yl benzylidene cyclododecane,
4'-[6-ethoxy carbonyl-1,5-dimethyl-1,3,5-hexatrien]-yl-2-benzylidene adamantane,
4'-[6-carboxy-1,5-dimethyl-1,3,5-hexatrien]-yl-2-benzylidene adamantane,
4'-[3-(4'-ethoxy carbonyl phenyl)-2-propen-yl]-2-benzylidene adamantane,
4'-[3-(4'-carboxy phenyl)-2-propen]-yl-2-benzylidene adamantane,
3-[5-(4'-methoxy carbonyl phenyl)-4-methyl-2,4-pentadien]-ylidene-2,2-dimethyl norbornane,
3-[5-(4'-carboxy phenyl)-4-methyl-2,4-pentadien]-ylidene-2,2-dimethyl norbornane,
4'-[4-ethylaminocarbonyl-3-methyl-1,3-butadien]-yl-2-benzylidene adamantane,
4'-[(2-ethyl)-4-hexylaminocarbonyl-3-methyl-1,3-butadien]-yl-2-benzylidene adamantane,
4'-[(di-0-1,2,3,4,5-isopropylidene)-4-D-galacto pyranosyloxy-3-methyl-1,3-butadien]-yl-2-benzylidene adamantane,
4'-[4-ethoxycarbonyl-1,3-butadien]-yl-2-benzylidene adamantane,
4'-[4-carboxy-1,3-butadien]-yl benzylidene adamantane,
4'-[(1-ethoxycarbonyl-3-methylthio)-4-propylaminocarbonyl-3-methyl-1,3-butadien]-yl-2-benzylidene adamantane and
3-[3-(4'-ethylaminocarbonyl phenyl)-2-propen]-ylidene-2,2-dimethyl norbornane.

18. A compound of claim 13 selected from the group consisting of: 2-[4'-ethoxy carbonyl] benzylidene adamantane,
2-[4'-carboxy] benzylidene adamantane,
2-[4'-formyl] benzylidene adamantane,
2-[4'-ethoxy carbonyl] benzylidene norbornane,
2-[4'-formyl] benzylidene norbornane,
2-[4'-ethoxy carbonyl] benzylidene cyclododecane,
2-[4'-hydroxymethyl] benzylidene cyclododecane,
2-[4'-formyl] benzylidene cyclododecane and
2-[4'-methylcarbonyl] benzylidene adamantane.

19. The derivative of claim 1 wherein Z represents a cyclododecane residue.

* * * * *